(12) United States Patent
Liu et al.

(10) Patent No.: US 12,178,422 B2
(45) Date of Patent: Dec. 31, 2024

(54) PROGRAMMABLE STIFFNESS TISSUE DISPLACEMENT DEVICE

(71) Applicant: The Regents of the University of California, Oakland, CA (US)

(72) Inventors: Shanglei Liu, La Jolla, CA (US); Mohamad Ramzi Abdul Majit, La Jolla, CA (US); Santiago Horgan, La Jolla, CA (US); Michael Tolley, La Jolla, CA (US); William Weston-Dawkes, La Jolla, CA (US); Esmeralda Ochoa, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 303 days.

(21) Appl. No.: 17/894,861

(22) Filed: Aug. 24, 2022

(65) Prior Publication Data
US 2022/0401095 A1    Dec. 22, 2022

Related U.S. Application Data

(62) Division of application No. 16/624,844, filed as application No. PCT/US2018/039044 on Jun. 22, 2018, now Pat. No. 11,504,108.

(Continued)

(51) Int. Cl.
*A61B 17/02* (2006.01)
*A61B 17/00* (2006.01)

(52) U.S. Cl.
CPC ............ *A61B 17/0218* (2013.01); *A61B 2017/00544* (2013.01); *A61B 2017/00557* (2013.01);

(Continued)

(58) Field of Classification Search
CPC ...... A61B 17/0218; A61B 2017/00544; A61B 2017/00557; A61B 2017/00566; A61B 2017/00858; A61B 2017/00946
See application file for complete search history.

(56) References Cited

U.S. PATENT DOCUMENTS

2009/0137984 A1    5/2009 Minnelli
2009/0192360 A1*   7/2009 Riess ............... A61B 17/02
                                                        600/210

(Continued)

OTHER PUBLICATIONS

International Search Report and Written Opinion dated Sep. 4, 2018, from application No. PCT/US2018/039044.

(Continued)

*Primary Examiner* — Sameh R Boles
(74) *Attorney, Agent, or Firm* — Foley & Lardner LLP

(57) ABSTRACT

A retraction device, e.g., a programmable stiffness state tissue displacement device, for providing increased visibility during an operation is provided. The device includes one or more strips of compliant jammable layer components connected in parallel, and encapsulated within a flexible envelope such that each of the one or more strips of compliant jammable layer components are pneumatically connected. The device further includes a negative pressure pump coupled to the flexible envelope, such that the application of negative pressure to the flexible envelope by the negative pressure pump causes the one or more strips of compliant jammable layer components to jam and thereby transition the retraction device from a malleable state to a rigid state.

7 Claims, 22 Drawing Sheets

Related U.S. Application Data

(60) Provisional application No. 62/524,034, filed on Jun. 23, 2017.

(52) U.S. Cl.
CPC ............... *A61B 2017/00566* (2013.01); *A61B 2017/00858* (2013.01); *A61B 2017/00946* (2013.01)

(56) References Cited

U.S. PATENT DOCUMENTS

| | | |
|---|---|---|
| 2009/0299343 A1 | 12/2009 | Rogers |
| 2012/0046525 A1 | 2/2012 | Russell et al. |
| 2014/0277384 A1 | 9/2014 | Melsheimer |
| 2014/0314976 A1 | 10/2014 | Niiyama et al. |
| 2015/0107233 A1 | 4/2015 | Ou et al. |
| 2015/0369325 A1 | 12/2015 | Bureau et al. |
| 2017/0035404 A1 | 2/2017 | Foster et al. |

OTHER PUBLICATIONS

U.S. Non-Final Office Action dated Jan. 4, 2022, from U.S. Appl. No. 16/624,844.

U.S. Notice of Allowance dated May 10, 2022, from U.S. Appl. No. 16/624,844.

\* cited by examiner

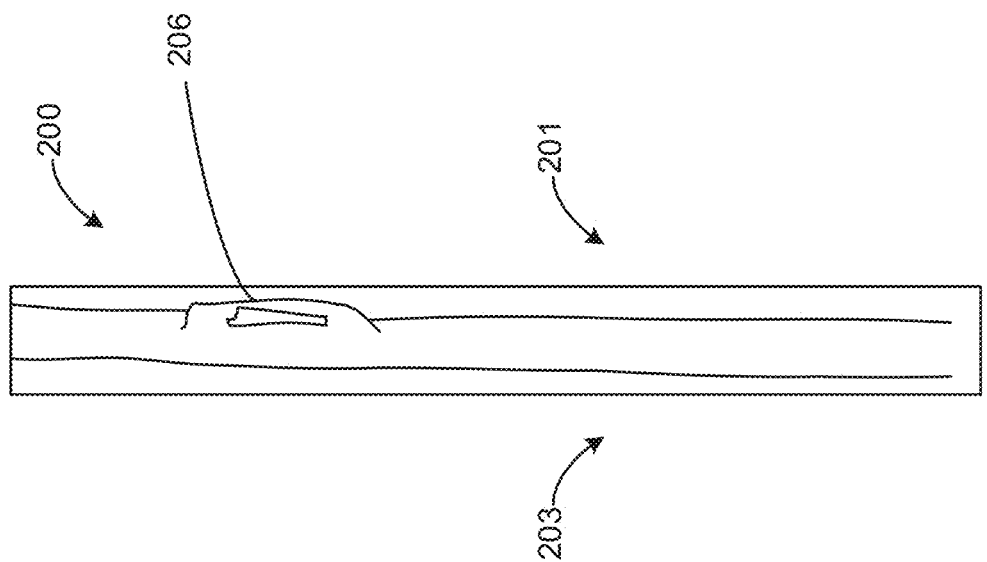

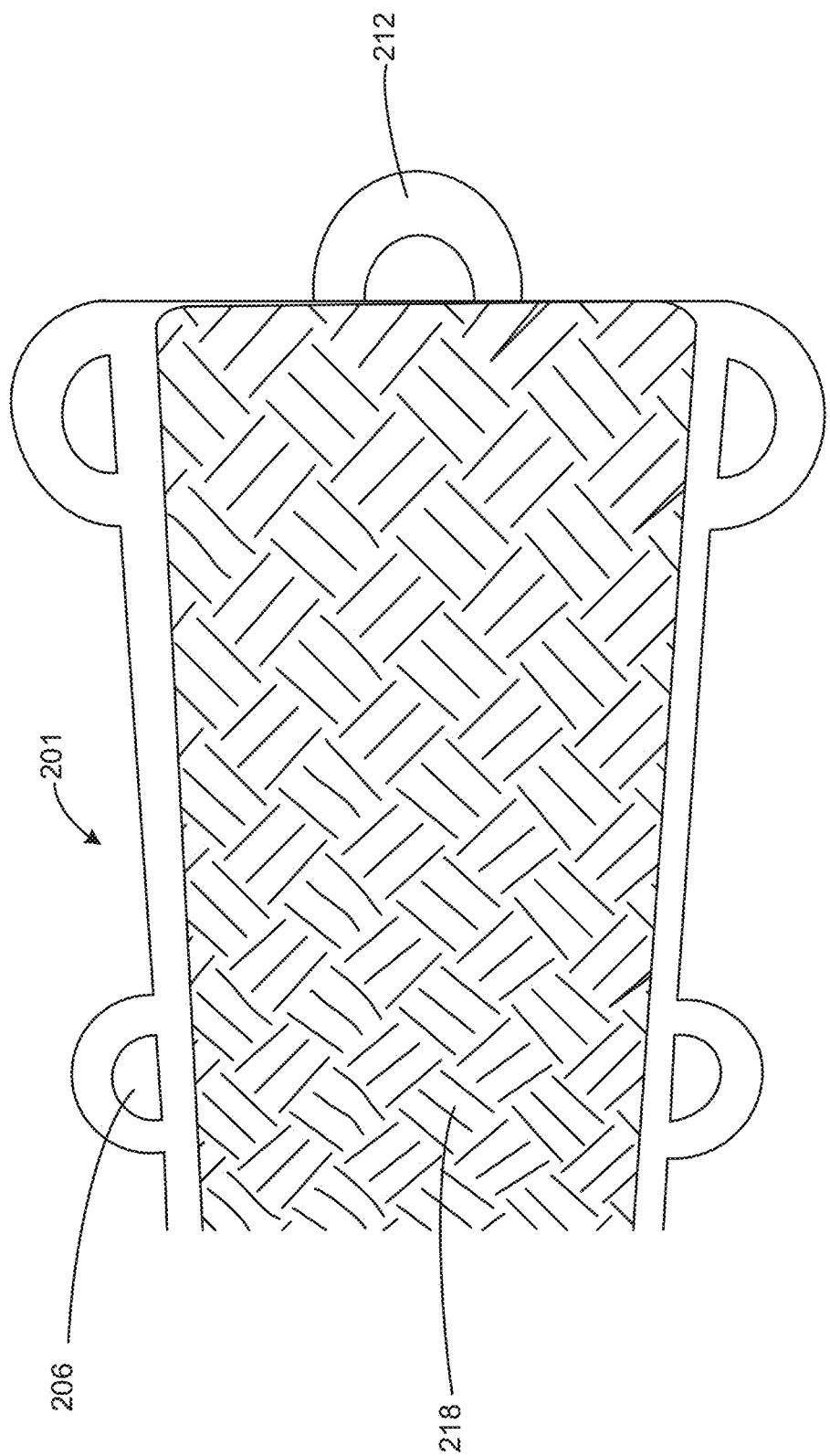

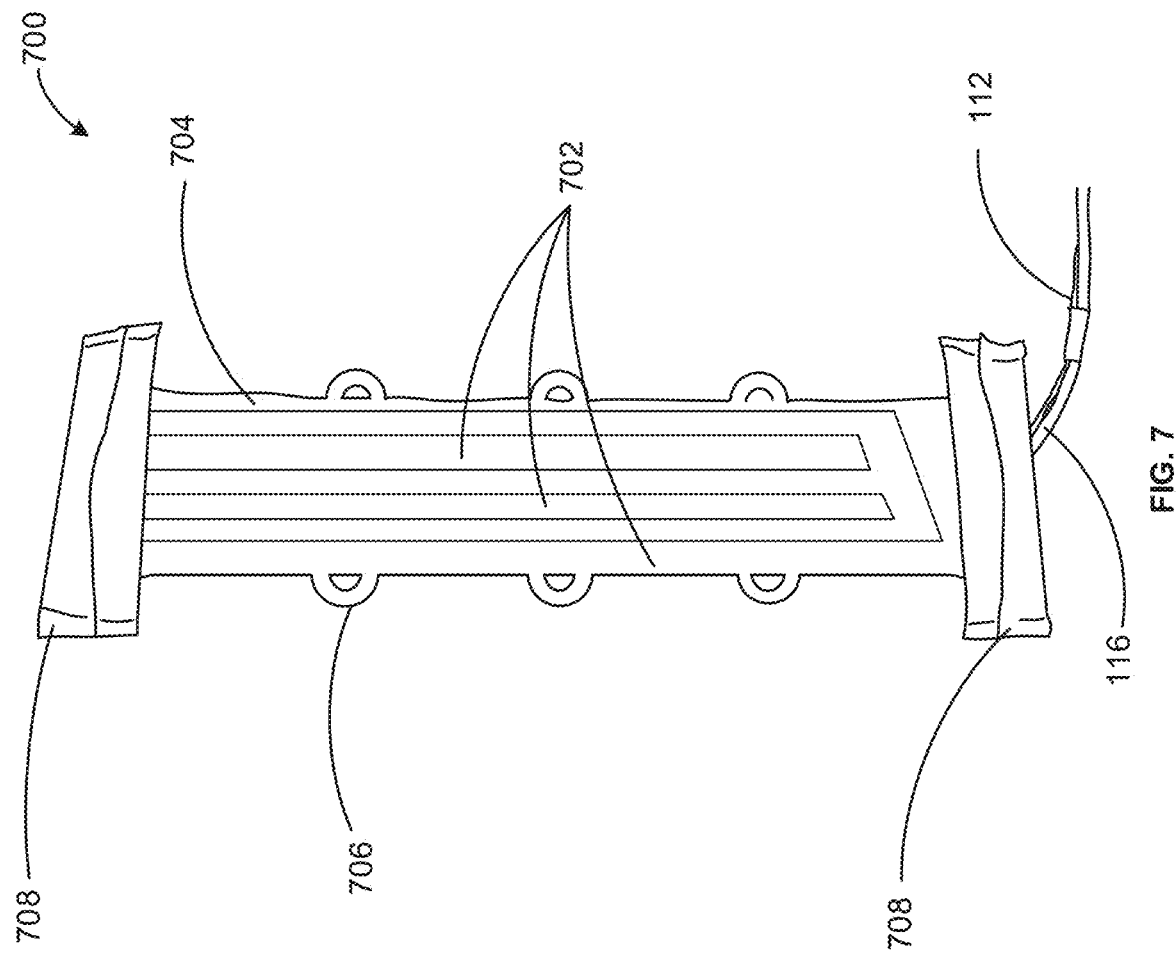

PROGRAMMABLE STIFFNESS TISSUE DISPLACEMENT DEVICE

CROSS-REFERENCE TO RELATED APPLICATION

The present application is a divisional of U.S. patent application Ser. No. 16/624,844, filed Dec. 19, 2019, which is a U.S. national stage application under 35 U.S.C. § 371 of International Application No. PCT/US2018/039044, filed Jun. 22, 2018, which in turn claims priority of U.S. Provisional Patent Application No. 62/524,034, filed Jun. 23, 2017, the entire contents of each of which are incorporated herein by reference in their entireties.

FIELD OF USE

The present disclosure is directed to a retraction device and methods for providing increased visibility during an operation.

BACKGROUND

Minimally Invasive Surgery (MIS) is a field of surgery that continues to look for new ways to perform surgery while reducing trauma to the normal physiologic barriers in the human body. Trends in MIS have long been moving toward fewer incision and minimizing trocar usage to reduce tissue trauma and improve outcomes. Although great progress has been made through the use of fewer trocar surgical systems, the technology seems to have hit a plateau in the number of entry sites into the abdomen required to provide assistance and retraction.

Previous solutions require either smaller incisions to be made into the abdomen or require dangerous hooks and lines to be introduced into the abdomen to suspend organs. Yet there is often a tradeoff between the number of available tools for retraction and the assistance available when reducing the number of entry sites into the abdomen. People have tried to combat this problem with small size percutaneous graspers (Teleflex MiniLap) or intra-abdominal retractions involving hanging cables (Aesculap Cinch, VersaLifter/Band, EndoGrab™/EndoLift™). However, these systems have not reached broad adoption for MIS mainly because they either require additional violation of the patient fascia or they are not intuitive to use.

For example, there are several types of tissue retractors in the market today. One is the Nathanson liver retractor which is a rigid retractor that requires anchoring onto the surgical gurney in addition to an incision placed into the abdomen. Additionally, Medtronic makes several laparoscopic retractors such as the EndoRetract, which is a hand held retractor that takes up an entire laparoscopic port in order to be introduced and held in place by a member of the surgical team. In open surgery, a whole variety of surgery retractors exist; however, these retractors are nearly all metal, e.g., steel, based retractors that require either mechanical fixture to the surgical gurney or require a member of the surgical team to be continuously holding it.

In view of the foregoing drawbacks of previously known apparatus and methods, there exists a need for a hands free surgical retractor that does not require additional incision(s) to be introduced into the surgical field.

SUMMARY

The present disclosure overcomes the drawbacks of previously-known systems by providing a retraction device, e.g., a programmable stiffness state tissue displacement device, and methods for providing increased visibility during an operation. The retraction device may include one or more strips of compliant jammable layer components. The one or more strips of compliant jammable layer components may be connected in parallel, and encapsulated within a flexible envelope such that each of the one or more strips of compliant jammable layer components are pneumatically connected. The retraction device further may include a negative pressure pump coupled to the flexible envelope. The negative pressure pump applies negative pressure to the flexible envelop such that the application of negative pressure to the flexible envelope causes the one or more strips of compliant jammable layer components to jam and thereby transition the retraction device from a malleable state to a rigid state. The negative pressure pump is coupled to the flexible envelope via a negative pressure pump tube, wherein the negative pressure pump tube has a first end coupled to a port in fluid communication with the flexible envelope, and a second end coupled to the negative pressure pump.

For example, in the malleable state, the one or more strips of compliant jammable layer components may be manipulated to a shape such that the retraction device may be introduced through a trocar. The retraction device further may include one or more handles sized and shaped to assist in manipulation of the retraction device, e.g., within the patient. In addition, in the rigid state, the one or more strips of compliant jammable layer components may have a stiffness sufficient to retract an anatomical structure of the patient to provide increased visibility during the operation. The retraction device may include a tapered end portion shaped to facilitate introduction of the retraction device through the trocar.

The retraction device further may include an inflatable positive pressure chamber disposed along at least a portion of the retraction device adjacent the flexible envelope. The inflatable positive pressure chamber is coupled to a positive pressure pump such that the positive pressure pump applies positive pressure to the inflatable positive pressure chamber. For example, the inflatable positive pressure chamber may receive positive pressure in an amount sufficient to transition the retraction device from a delivery state to an expanded state. The inflatable positive pressure chamber also may receive positive pressure in an amount that increases friction force between the retraction device and an adjacent anatomical structure. The positive pressure pump is coupled to the inflatable positive pressure chamber via a positive pressure pump tube, wherein the positive pressure pump tube has a first end coupled to a port in fluid communication with the inflatable positive pressure chamber, and a second end coupled to the positive pressure pump.

In one embodiment, the inflatable positive pressure chamber is an inflatable pneumatic pouch coupled to an end portion of the retraction device. The inflatable pneumatic pouch receives positive pressure therein such that the inflatable pneumatic pouch ensures safe contact with surrounding tissue while maintaining a desired shape.

The retraction device further may include a high-friction surface having a tread design that provides additional traction between the retraction device and an adjacent anatomical structure. For example, the high-friction surface may be a rubber tape having an adhesive.

In accordance with another aspect of the disclosure, a method for providing increased visibility during an operation is provided. The method may include introducing a retraction device in a delivery state to an operation site within a patient, wherein the retraction device includes one or more strips of compliant jammable layer components. The one or more strips of compliant jammable layer components are connected in parallel and encapsulated within a flexible envelop. The method further includes manipulating the one or more strips of compliant jammable layer components to a desired shape, and applying negative pressure to the flexible envelope to jam the one or more strips of compliant jammable layer components such that the retraction device transitions from a malleable state to a rigid state. For example, in the rigid state, the retraction device may have a stiffness sufficient to retract an anatomical structure of the patient to provided increased visibility during the operation.

In one embodiment, the retraction device further includes an inflatable positive pressure chamber disposed along at least a portion of the retraction device adjacent the flexible envelope. Accordingly, the method may include applying positive pressure to the inflatable positive pressure chamber after introducing the retraction device, such that the retraction device transitions from the delivery state to an expanded state at the operation site within the patient. The method further may include deflating the inflatable positive pressure chamber prior to manipulating the one or more strips of compliant jammable layer components to the desired shape. In addition, the method further includes applying positive pressure to the inflatable positive pressure chamber after manipulating the one or more strips of compliant jammable layer components to the desired shape to increase normal forces on a surface of the retraction device, thereby increasing friction forces between the retraction device and the anatomical structure of the patient. The method further may include deflating the inflatable positive pressure chamber after applying negative pressure to the flexible envelope, thereby providing stronger retraction of the anatomical structure of the patient during the operation.

In another embodiment, the retraction device further includes a tapered end portion shaped to facilitate introduction through a trocar. Accordingly, the method further includes removing the retraction device by pulling the retraction device through the trocar via the tapered end portion.

BRIEF DESCRIPTION OF THE DRAWINGS

FIGS. 2A-E illustrate an exemplary retraction device constructed in accordance with the principles of the present disclosure.

FIG. 7 illustrates another exemplary retraction device constructed in accordance with the principles of the present disclosure.

DETAILED DESCRIPTION

The retraction device described herein preferably helps surgeons operate by physically displacing organs and tissues for increased visibility during an operation. The retraction device may be manipulated into various shapes for various applications, and may be scalable for open surgery and minimally invasive surgery. By changing the stiffness of the structure of the retraction device, both a compliant/malleable state for insertion/shaping and rigid state to support organs and tissues during surgery may be achieved. For example, the retraction device may be manipulated for insertion for minimally invasive surgery through a trocar in the malleable state, and support an anatomical structure away from the operating zone in the rigid state. Additionally, the retraction device does not require additional incisions for insertion, nor a member of the surgical team to continuously hold the device in place, thus potentially freeing up additional operating room resources.

Figure 1A:
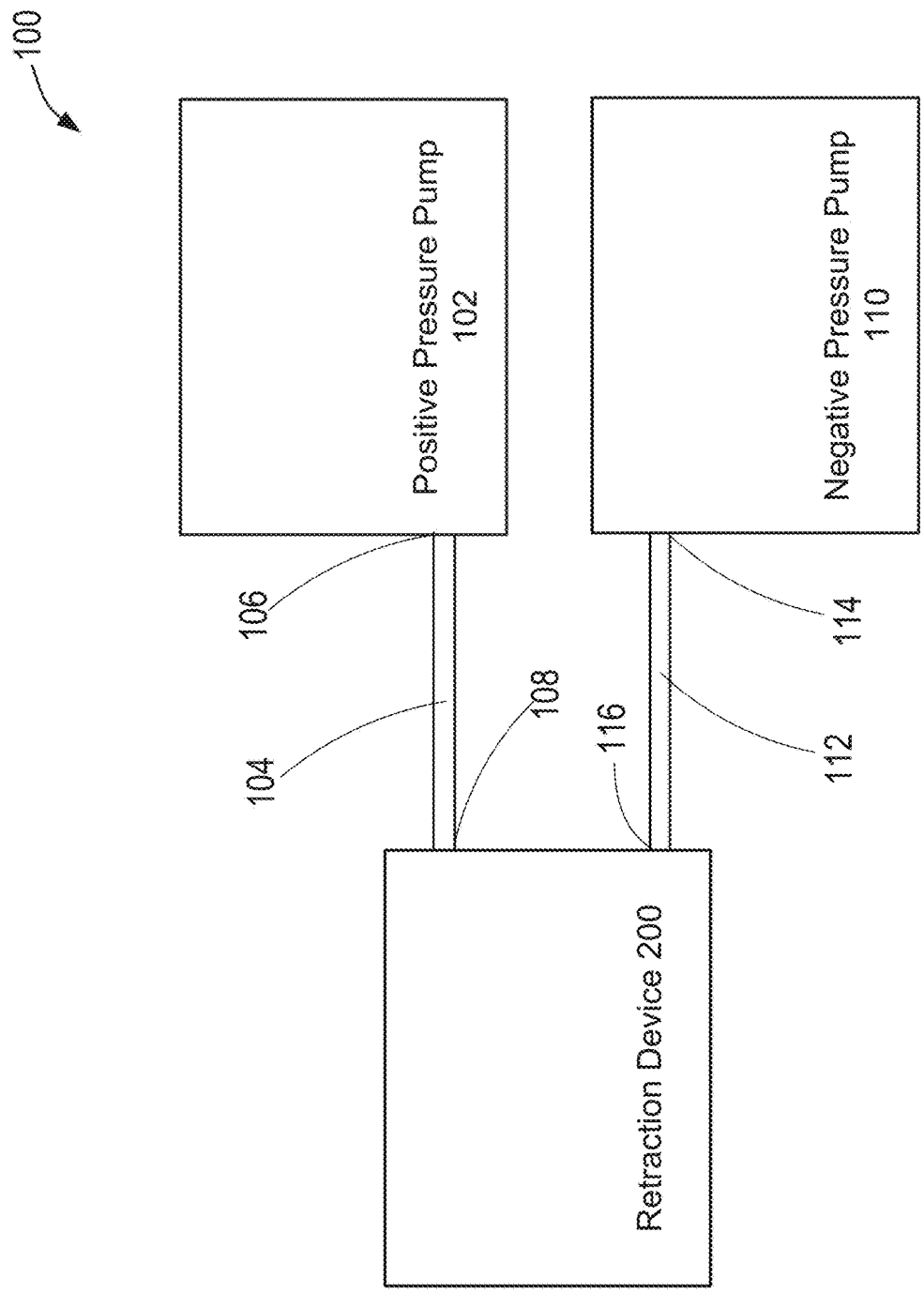
FIG. 1A illustrates a schematic of an exemplary system for providing increased visibility during an operation in accordance with the principles of the present disclosure.

Referring now to FIG. 1A, an exemplary system for providing increased visibility during an operation is described. System 100 includes retraction device 200 coupled to positive pressure pump 102 via tubing 104. For example, proximal end 106 of tubing 104 may be coupled to positive pressure pump 102, and distal end 108 of tubing 104 may be coupled to an opening port of retraction device 100, such that positive pressure pump 102 may apply positive pressure to retraction device 200 via tubing 104. In addition, retraction device 200 is coupled to negative pressure pump 110 via tubing 112. For example, proximal end 114 of tubing 112 may be coupled to negative pressure pump 110, and distal end 116 of tubing 112 may be coupled to another opening port of retraction device 100, such that negative pressure pump 110 may apply negative pressure to retraction device 200 via tubing 112. Retraction device 200 is structured to transition between a malleable state and a rigid state upon application of negative pressure by negative pressure pump 110.

Figure 1B:
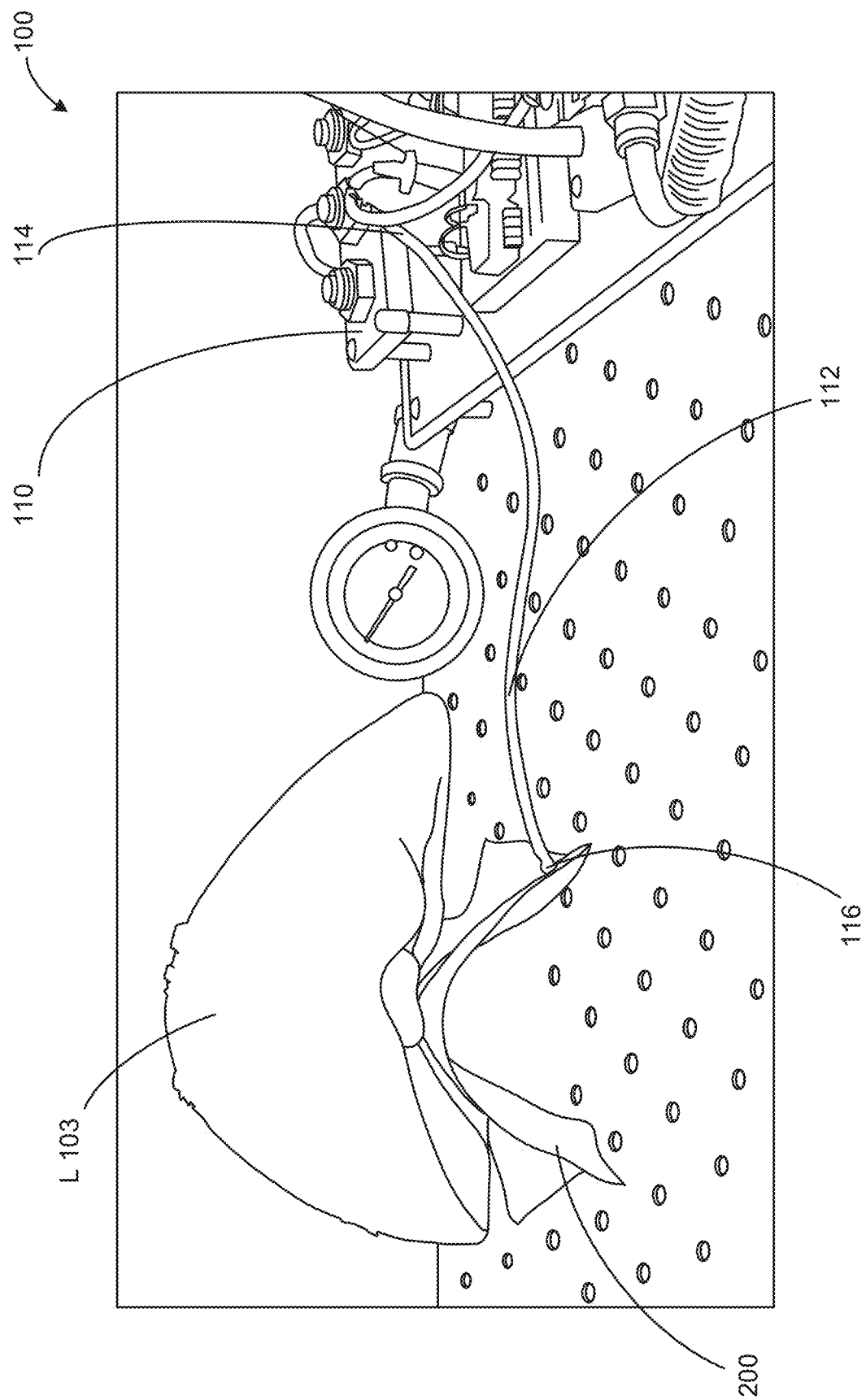
FIG. 1B illustrates an exemplary system for providing increased visibility during an operation in accordance with the principles of the present disclosure.

Referring now to FIG. 1B, an exemplary example of system 100 is described. As shown in FIG. 1B, negative pressure pump 110 may apply negative pressure to retraction device 200 via proximal end 114 and distal end 116 of tube 112 to thereby retain retraction device 200 in a rigid state such that retraction device 200 retracts an anatomical structure of a patient, e.g., liver L. In one embodiment, retraction device 200, in the rigid state, is designed to yield to forces that if resisted, would cause injury to the anatomical structure of the patient. As the liver L is retracted, the surgeon is provided increased visibility during an operation. Additionally, as retraction device 200 does not require the surgeon to hold onto it, the surgeon may use both hands during the operation.

Figure 2A:
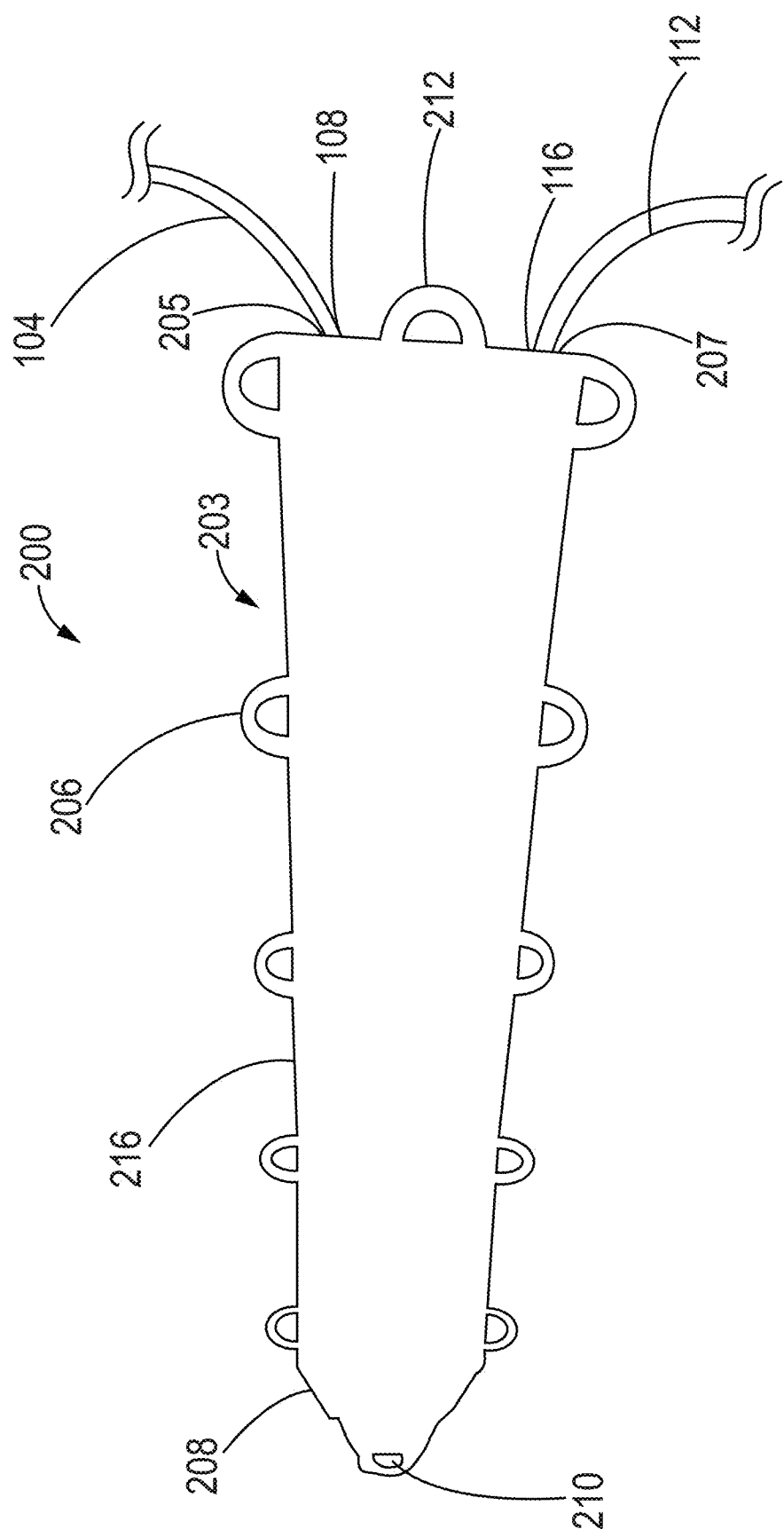

Referring now to FIGS. 2A-2E, an exemplary retraction device is described. Retraction device 200 is designed with the ability to change stiffness states without changing size, adding anchors to equipment's outside the human body, needing additional surgical personnel to maintain retraction during surgery, or introducing any additional material. FIG. 2B is a side view of a portion of retraction device 200. As shown in FIG. 2B, retraction device 200 includes top surface 201 and bottom surface 203.

Figure 2C:
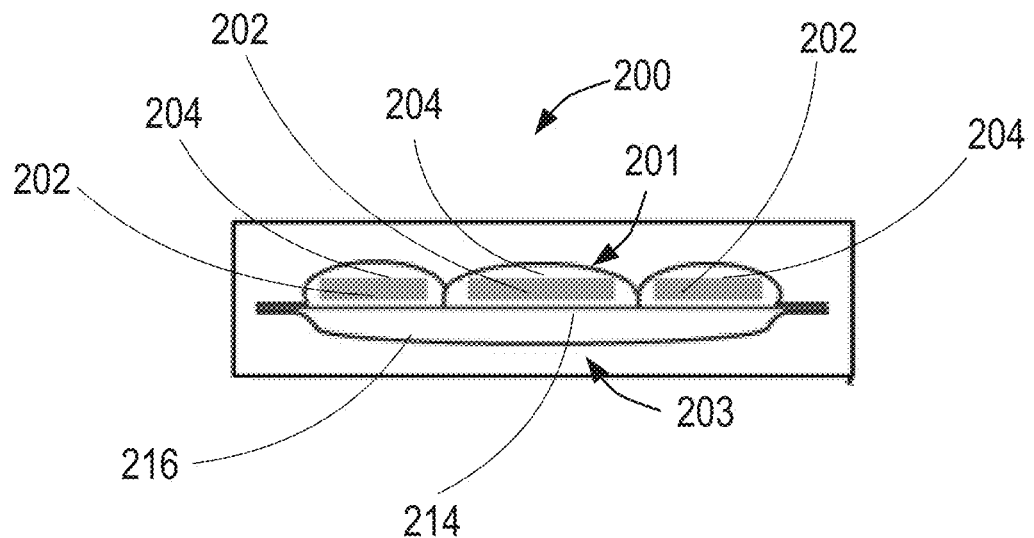

Retraction device 200 includes one or more strips of compliant jammable layer components 202. For example, FIG. 2C illustrates retraction device 200 having three strips of compliant jammable layer components. FIG. 2C is a cross-sectional view of retraction device 200. Each strip of compliant jammable layer components 202 is connected in parallel and may be rolled into a narrow tube. All parallel sections including each strip of compliant jammable layer components 202 are encapsulated in flexible envelope 204, and are pneumatically connected. Flexible envelope 204 is in fluid communication with negative pressure pump 110 via port opening 207 coupled to flexible envelope 204 such that distal end 116 of tube 112 is coupled to port opening 207.

Upon the application of negative pressure by negative pressure pump 110, a high normal force is exerted by atmospheric pressure (maximum of 101.325 KPa at sea level) through flexible envelope 204. This causes the layers of each strip of compliant jammable layer components 202 to be pushed together and prevent relative motion, initiating the transition from a flexible/malleable state to a rigid state, due to the intentionally high static friction of the material sheets of the layers. This principle, known as "layer jamming," allows retraction device 200 to transition from the flexibility of paper to the stiffness of a composite beam.

Layer jamming enables tunable stiffness in thin and lightweight sheet materials. It is accomplished when these materials are placed in a vacuum inside an airtight envelope. The material within the envelope transitions from a flexible state to a rigid state by isothermal phase change, or "jamming" of the layers. The external pressure induced by the internal vacuum causes a high frictional force between the layers making them transition from the flexibility of paper to the stiffness of a composite beam. The layers of each component are adhered together at one end and these components are slipped within each other to create the interleaved portion. These layers can be chosen of a range of materials (e.g. paper, silk, sand paper) to create the desired initial compliance. Furthermore, the coefficient of friction of these materials will determine the final stiffness of the activated laminate. A flexible and compliant material (e.g. biologically inert silicone) is sealed around these layers to create an airtight envelope. A pneumatic adapter is connected to a hole at one end of the envelope through which a vacuum can be applied. Other methods of jamming may be used including granular jamming and fiber jamming.

Jamming of retraction device 200 allows an organ within the body to be retracted, e.g., lifted, during laparoscopic surgery. Because retraction device 200 is malleable when unjammed, retraction device 200 may be folded or rolled in a delivery state such that retraction device 200 may be introduced through existing minimally invasive surgery trocars, natural orifices, or other small openings. This enables surgeons to introduce retraction device 200 into a body cavity without making large incisions and is able to manipulate retraction device 200 while it is in the malleable state. Once placed in an optimum location, vacuum may be applied, e.g., via negative pressure pump 110, to cause retraction device 200 to become jammed, and thus become a rigid retractor intra-abdominally.

For example, to lift and hold the liver in place, retraction device 200 needs to resist deformation due to the downward gravitational force of the liver. The liver has a mass of 1.5 kg and thus retraction device 200 would require a holding force of approximately 15 N. By conforming to the shape of the liver, retraction device 200 will avoid applying point loads that would lead to stress concentrations on the liver or surrounding organs. Retraction device 200 may be designed to yield to forces that if resisted, would cause injury to the patient.

As shown in FIG. 2A, retraction device 200 may include embedded handles 206 positioned along one or both sides of retraction device 200. Laparoscopic operation is facilitated by using embedded handles 206 for manipulation and color for orientation. Retraction device 200 further may include tapered end portion 208 shaped for facilitating introduction of retraction device 200 through a trocar as described in further detail below. Thus, retraction device 200 may include handle 210 positioned at the tip of tapered end portion 208. Retraction device 200 also may include handle 212 at an opposite end of retraction device 200 for further facilitating manipulation of retraction device 200. As will be understood by a person having ordinary skill in the art, both ends of retraction device 200 may include a tapered end portion such that retraction device 200 may be pulled through a trocar for removal from either end.

Referring again to FIG. 2C, retraction device 200 includes inflatable positive pressure chamber 216 disposed along bottom surface 203 of retraction device 200, adjacent at least a portion of flexible envelope 204 along retraction device 200. Inflatable positive pressure chamber 216 is separated from flexible envelope 204 via inner layer 214 of retraction device 200. Inflatable positive pressure chamber 216 is in fluid communication with positive pressure pump 102 via port opening 205 coupled to inflatable positive pressure chamber 216 such that distal end 108 of tube 104 is coupled to port opening 205. Inflatable positive pressure chamber 216 may receive positive pressure from positive pressure pump 102 via tube 104 in an amount sufficient to cause retraction device 200 to transition from a folded or rolled delivery state to an unfolded or unrolled expanded state. For example, when retraction device 200 is inserted into the operation site, e.g., the patient's abdomen, through a trocar in a rolled delivery state, inflatable positive pressure chamber 216 may receive positive pressure to cause it to unroll and straighten within the patient's abdomen. Inflatable positive pressure chamber 216 may then be deflated so the surgeon may continue the operation.

Inflatable positive pressure chamber 216 also may receive positive pressure from positive pressure pump 102 via tube 104 in an amount sufficient to apply additional pressure against the surrounding anatomical structures. By adding pressure to the surrounding anatomical structures, e.g., abdominal walls, the normal forces on top surface 203 of retraction device 200 increases, thereby increasing the friction forces between top surface 203 of retraction device 200 and the surrounding anatomical structures.

Figure 2D:
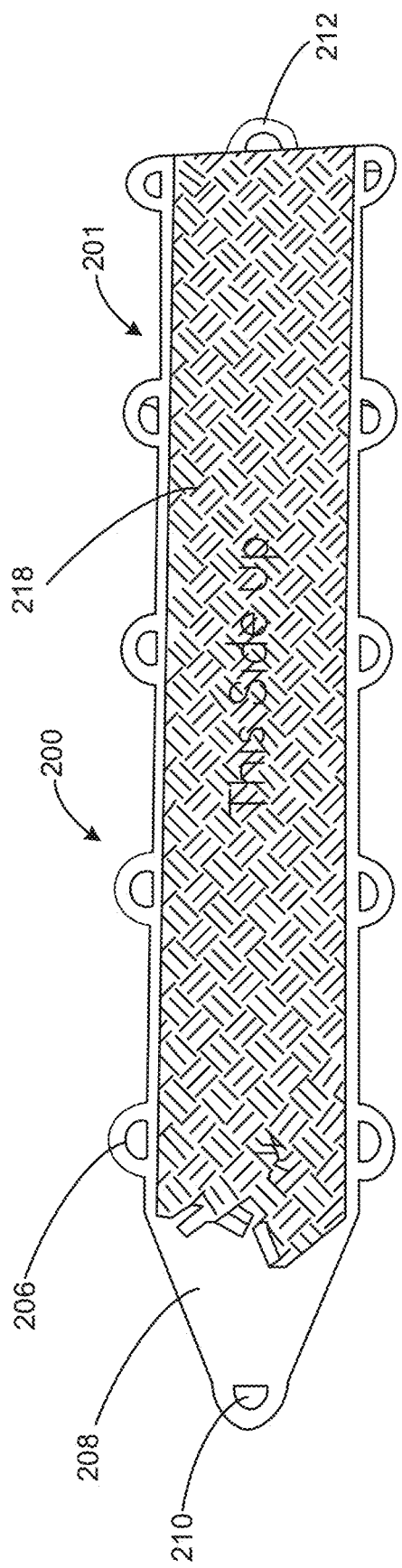

Referring now to FIGS. 2D and 2E, top surface 203 of retraction device 200 is described. Top surface 203 may include high-friction surface 218 such that high-friction surface 218 comes into direct contact with the retracted surrounding anatomical structures. High-friction surface 218 may be, for example, high-friction tape such as a rubber having an adhesive backing for adhering to top surface 201 of retraction device 200. As shown in FIGS. 2D and 2E, the exposed surface of high-friction surface 218 includes a tread design such that high-friction surface 218 provides additional traction, for example, in moist environments, between high-friction surface 218 of retraction device 200 and the surrounding anatomical structures. For example, during a gastric bypass operation, high-friction surface 218 of retraction device 200 comes into contact with the liver and abdominal walls and provides additional traction on the internal organs and tissue, thereby limiting movement of the organs, and providing improved adhesion to the abdominal walls to prevent perioperative movement. In addition, high-friction surface 218 provides a material contrast during use of retraction device 200 so that the surgeon is able to determine the orientation of the device.

Figure 3:
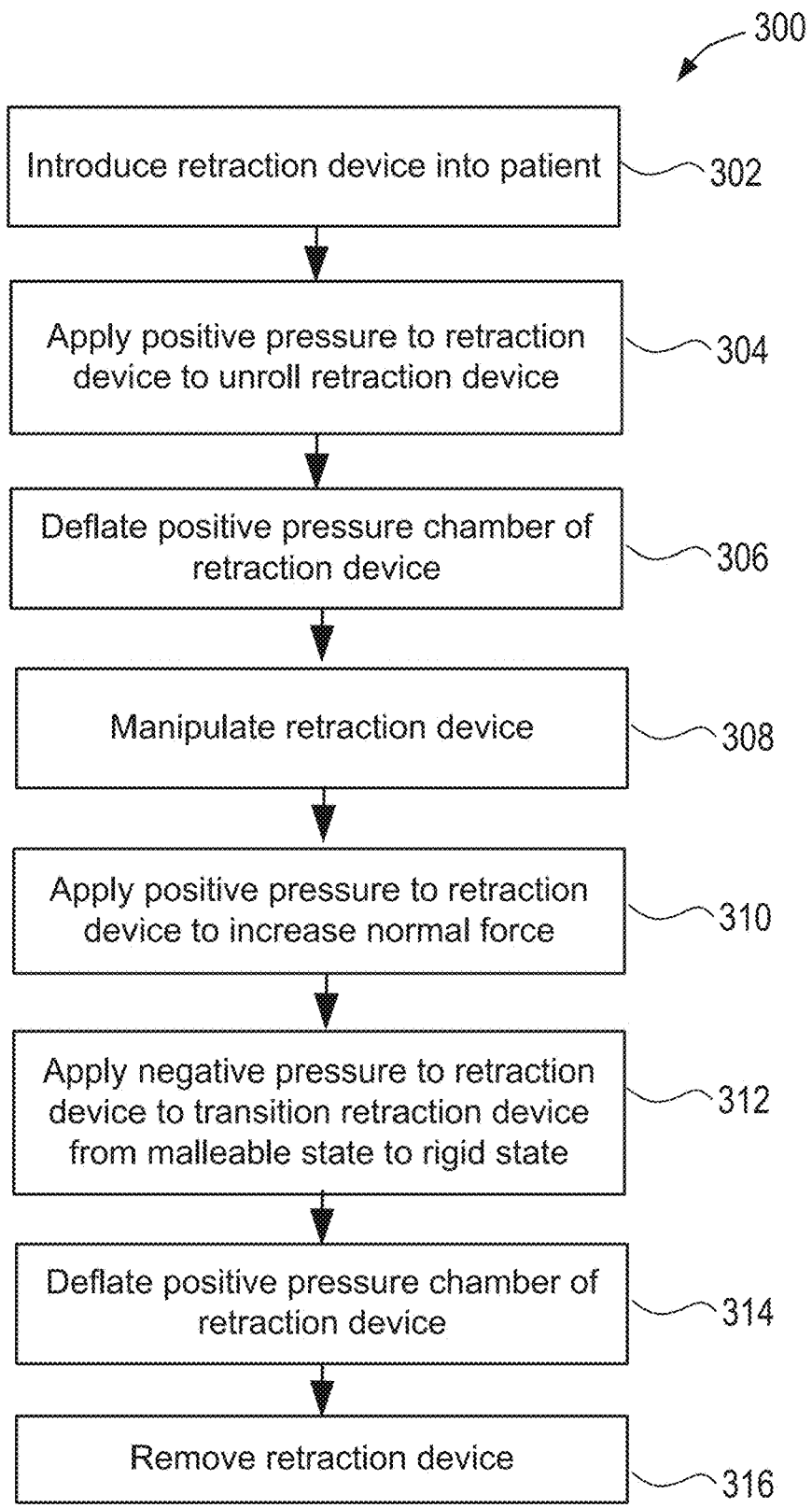
FIG. 3 is a flow chart illustrating an exemplary method for providing increased visibility during an operation in accordance with the principles of the present disclosure.

Referring now to FIG. 3, an exemplary method for providing increased visibility during an operation is described, with additional reference to FIGS. 4A-5A. Method 300 may be used for layer jamming to create a complete intra-corporeal retractor that can be introduced through a trocar and manipulated to the desired shape. At step 302, the retraction device is introduced into the patient. Because the retraction device is malleable when unjammed, it has been designed to fit through an existing trocar during surgery in a folded or rolled delivery state.

Figure 4A:
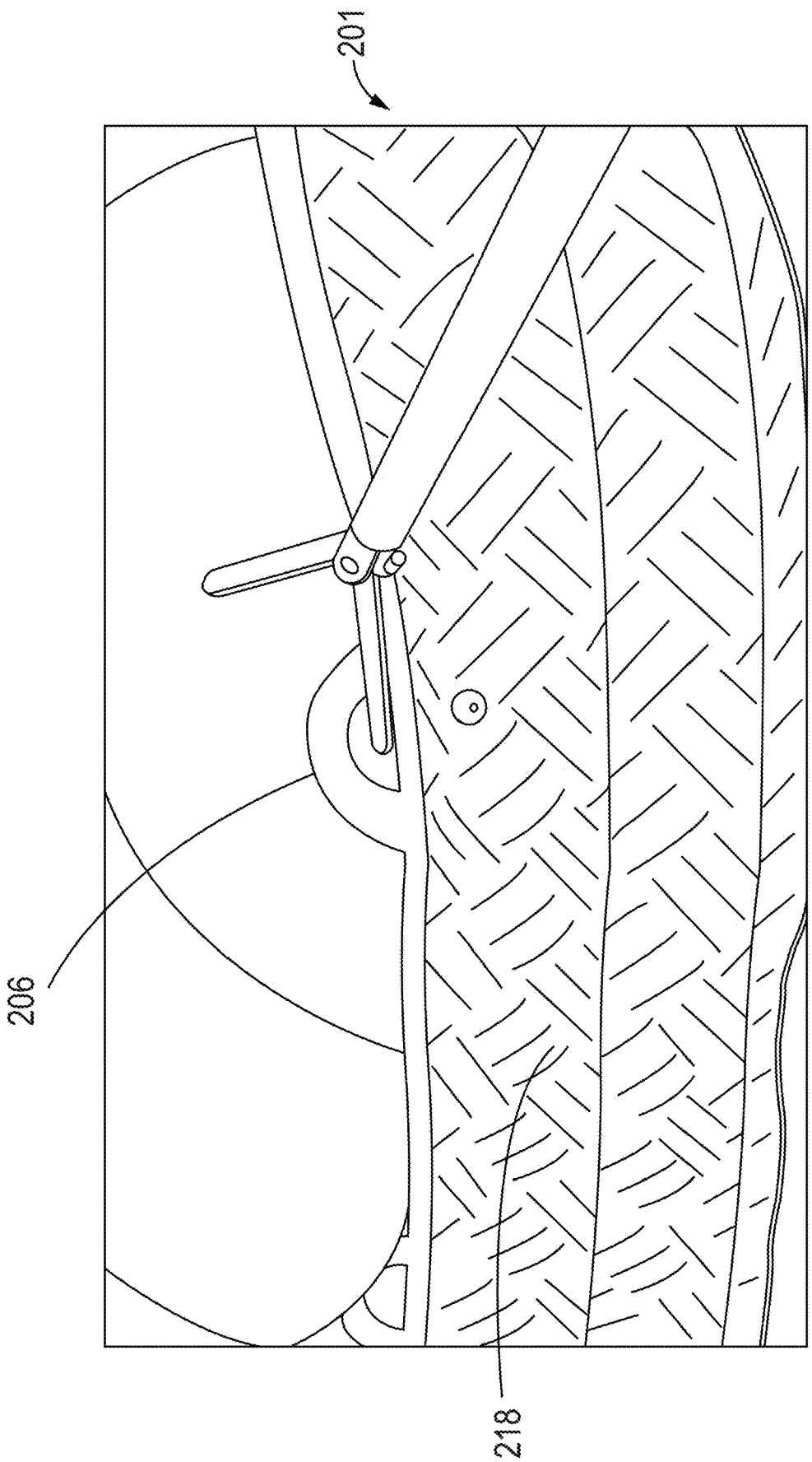
FIG. 4A illustrates the top surface of the retraction device of FIG. 2A during operation of the retraction device.
Figure 4B:
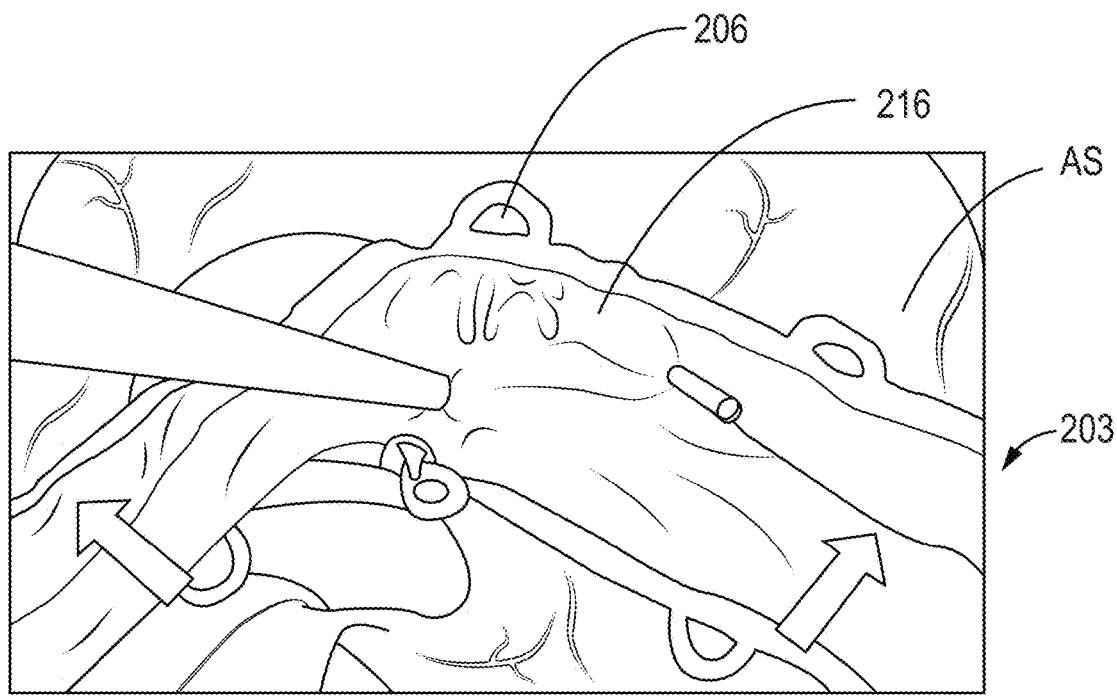
FIG. 4B illustrates normal forces on the surface of the retraction device of FIG. 2A during operation of the retraction device.

At step 304, positive pressure is applied to the inflatable positive pressure chamber of the retraction device such that the retraction device transitions from the folded or rolled delivery state to an unfolded or unrolled expanded state as shown in FIG. 4A. FIG. 4A illustrates high-friction surface 218 disposed on top surface 201 of retraction device 200 in an expanded state due to inflatable positive pressure chamber 216 receiving positive pressure from positive pressure pump 102. High-friction surface 218 is "upper facing" and contacts the surrounding anatomical structures during operation.

Referring back to FIG. 3, at step 306, the inflatable positive pressure chamber may be deflated, if necessary, such that the retraction device returns to a flat state where the surgeon may continue the operation. At step 308, the retraction device may be manipulated into the desired shape at the desired location, e.g., to retract an anatomical structure of the patient. Once placed in an optimum location, at step 310, positive pressure may be applied to the inflatable positive pressure chamber of the retraction device to increase normal forces on the surface of the retraction device as denoted by the arrows illustrated in FIG. 4B, thereby increasing friction forces between the retraction device and the anatomical structure of the patient.

Figure 4C:
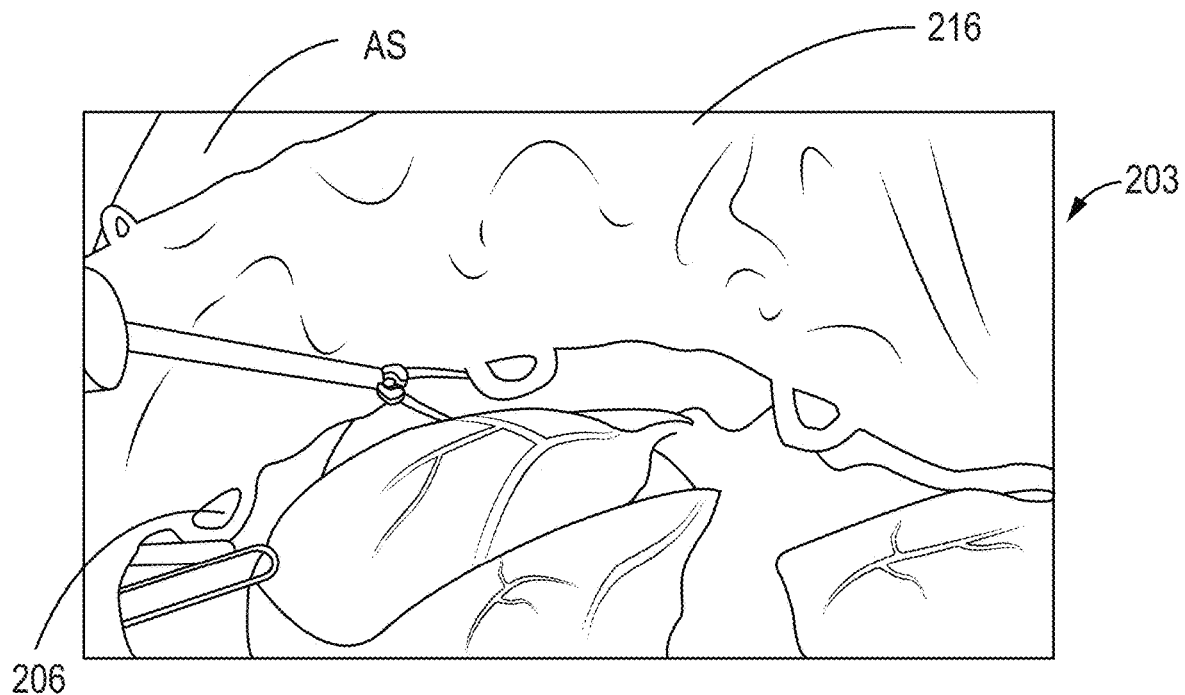
FIG. 4C illustrates the bottom surface of the retraction device of FIG. 2A during operation of the retraction device.

Referring back to FIG. 3, at step 312, negative pressure may be applied to the flexible envelope of the retraction device to cause the layers of each strip of compliant jammable layer components of the retraction device to become jammed, and thus become a rigid retractor intra-abdominally, e.g., transition from a malleable state to a rigid state as shown in FIG. 4C. FIG. 4C illustrates bottom surface 203 of retraction device 200 in a manipulated, expanded state such that retraction device 200 retracts the surrounding anatomical structures AS and provides increased visibility of the operation zone during the operation. By conforming to the shape of the liver, retraction device 200 will avoid applying point loads that would lead to stress concentrations on the liver or surrounding organs. The retraction device has also been designed to yield to forces that if resisted, would cause injury to the patient.

Figure 5A:
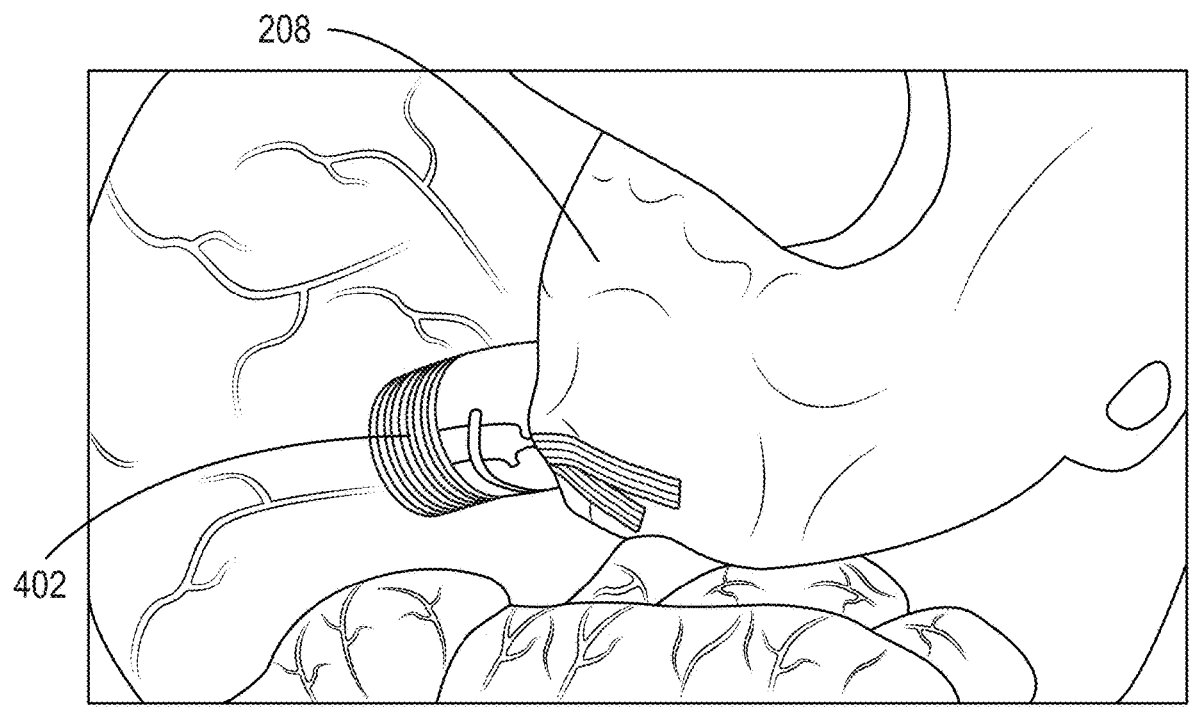
FIG. 5A illustrates removal of the retraction device of FIG. 2A in accordance with the principles of the present disclosure.
Figure 5B:
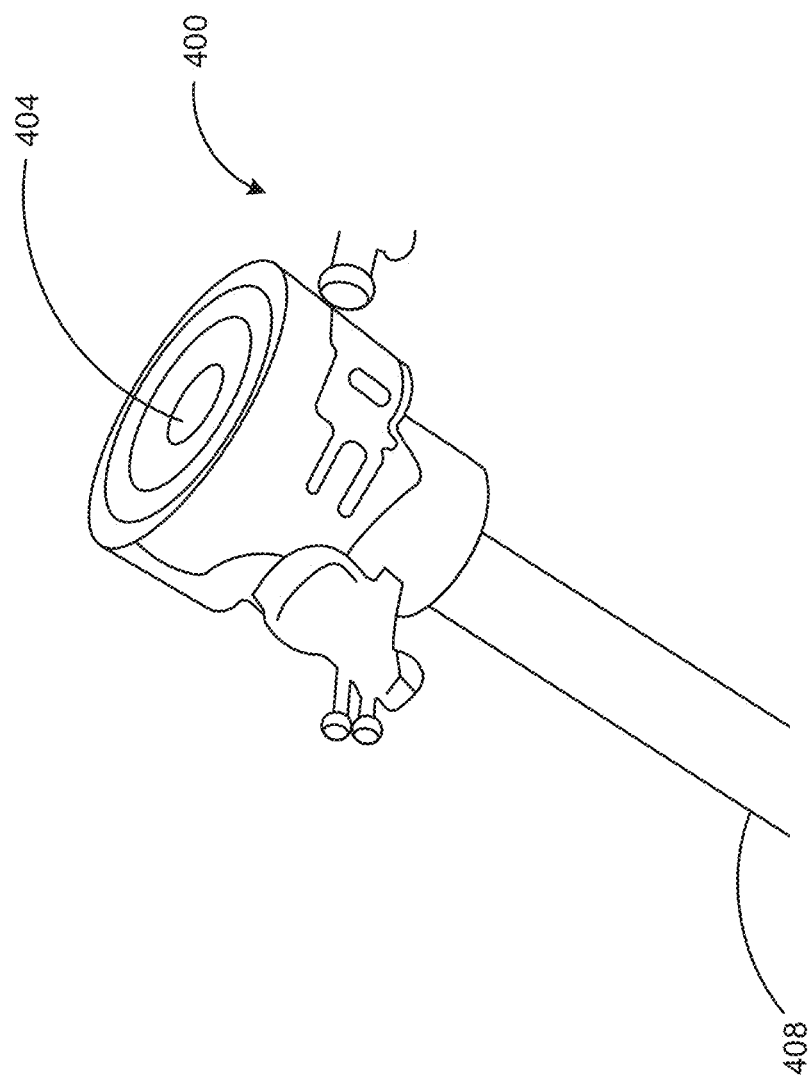
FIG. 5B illustrates an exemplary trocar for delivering and removing a retraction device in accordance with the principles of the present disclosure.

Referring back to FIG. 3, at step 314, the inflatable positive pressure chamber may be deflated while the flexible envelope is active which provides stronger retraction of the anatomical structures of the patient during the length of the operation, e.g., stronger anchorage to the abdominal walls. Then, retraction device 200 may be returned to its malleable state, and removed through the trocar at step 316 as illustrated in FIG. 5A. For example, retraction device 200 may be removed from the operation zone through trocar 400 illustrated in FIG. 5B. As shown in FIG. 5B, trocar 400 includes proximal end 404, distal end 408, and a lumen sized and shaped for receiving retraction device 200 in the folded or rolled delivery state extending therebetween. Distal end 408 has a cylindrical shape and may be cut at an angle such that it has a pointed tip. Distal end 408 along with the tapered end portion of the retraction device allow the retraction device to be efficiently folded and pulled through trocar 400 for removal as shown in FIG. 5A.

Figure 6A:
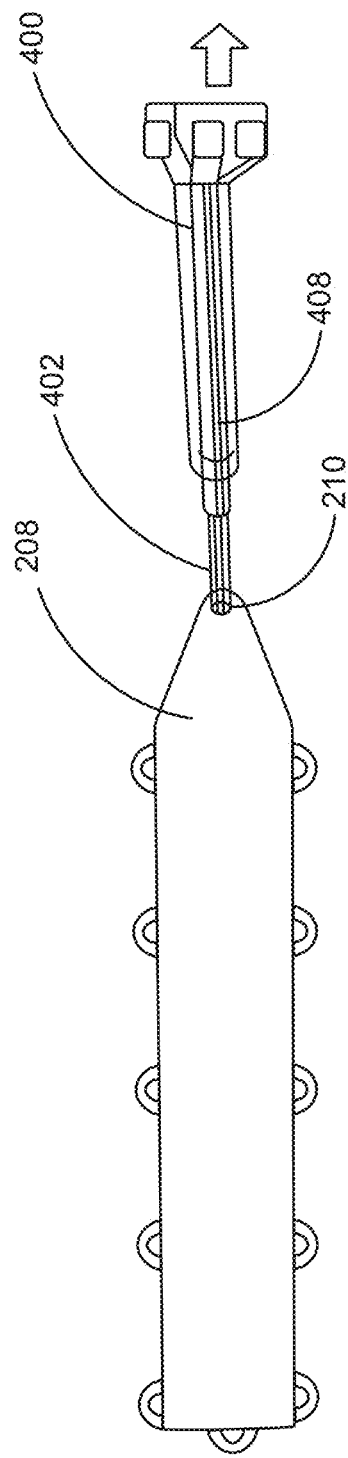
FIGS. 6A-6E illustrate the removal process of an exemplary retraction device through a trocar in accordance with the principles of the present disclosure.
Figure 6B:
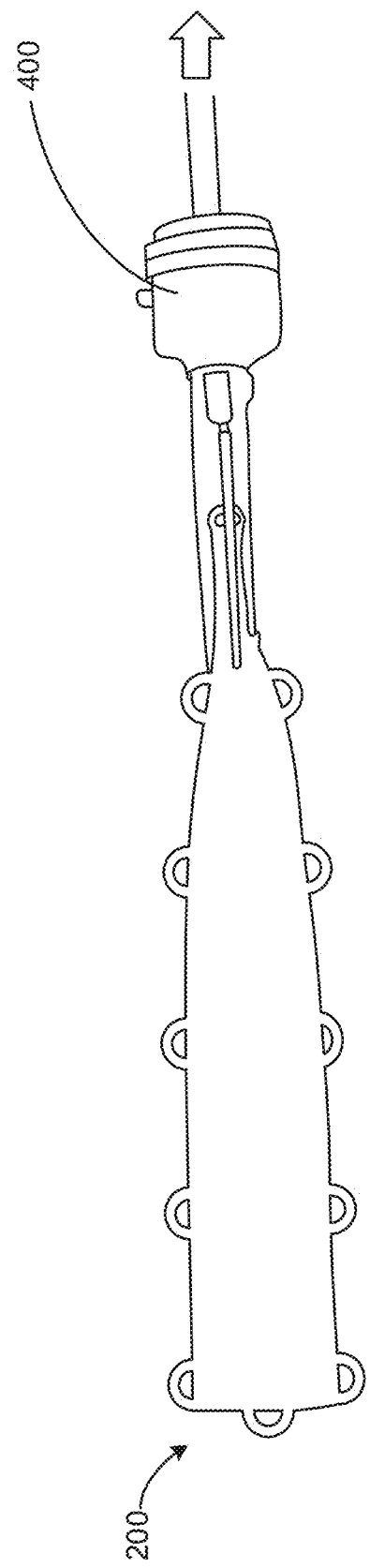
Figure 6C:
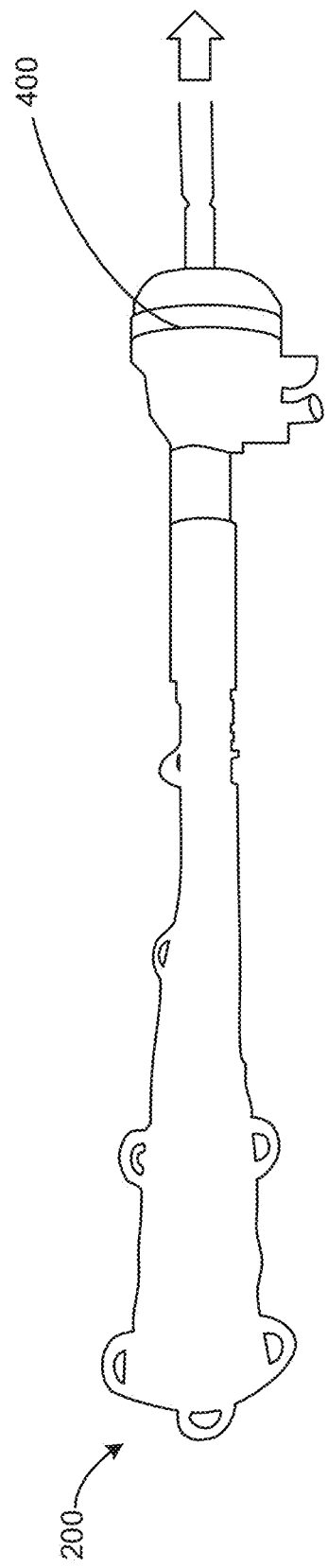
Figure 6D:
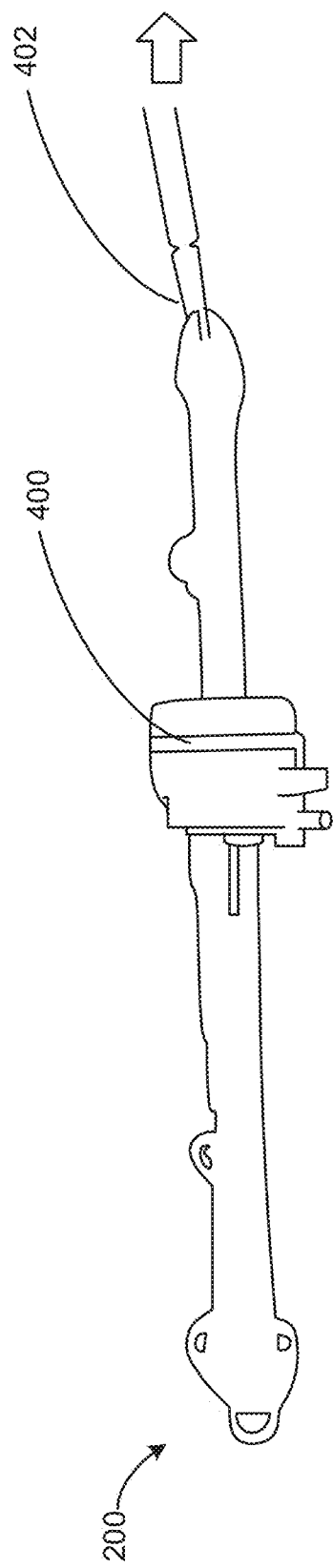
Figure 6E:
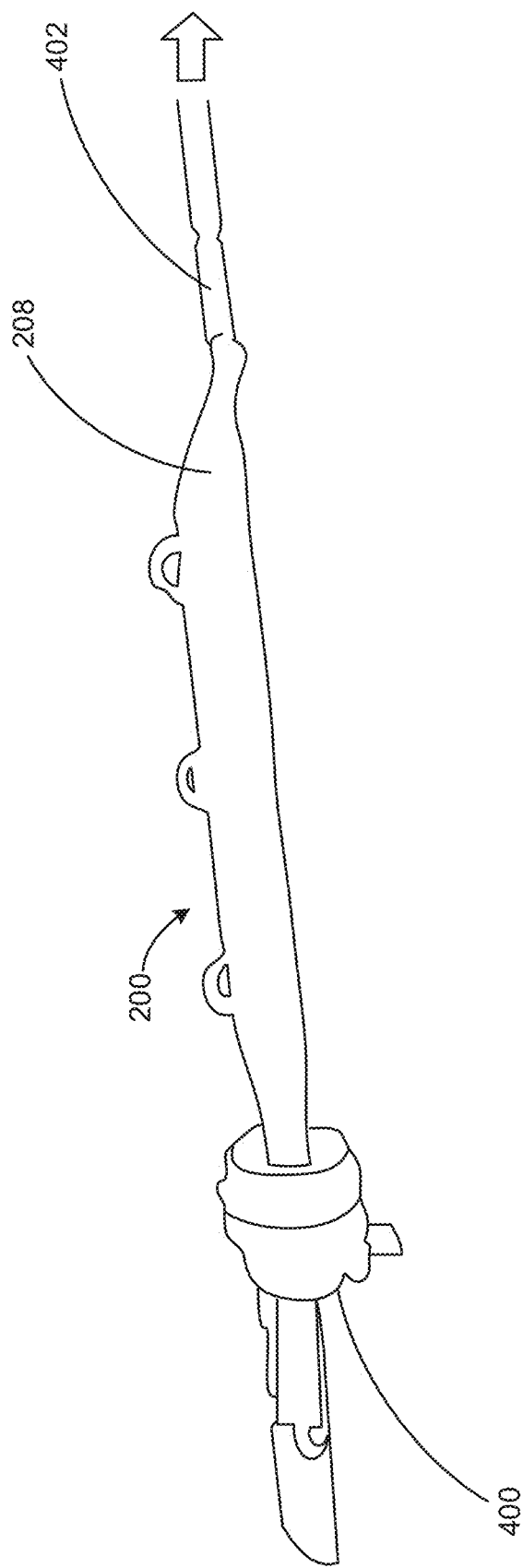

Referring now to FIGS. 6A-6E, removal of retraction device 200 through trocar 400 is illustrated. As shown in FIG. 6A, extraction device 402 is extended through the lumen of trocar 400 such that it is exposed beyond distal end 408 of trocar 400 to engage with handle 210 at tapered end portion 208 of retraction device 200. As shown in FIGS. 6B-6E, retraction device 200 is continuously pulled through trocar 400 until it is completely removed from the operation zone. As retraction device 200 is pulled through trocar 400, malleable retraction device 200 is folded such that it is sized for introduction through the lumen of trocar 400.

Referring now to FIG. 7, another exemplary retraction device is described. Retraction device 700 is constructed similar to retraction device 200 of FIG. 2A. In addition to or instead of an inflatable positive pressure chamber disposed along the bottom surface of the retraction device, retraction device 700 includes an inflatable positive pressure chamber, e.g., pneumatic pouch 708, at one or more ends of retraction device 700 adjacent at least a portion of flexible envelope 704. Embedded pneumatic channels coupled to a positive pressure pump are used to inflate pneumatic pouch 708 on either end of the retraction device 700. This provides support for retraction device 700, while safely contacting surrounding tissues during the operation while maintaining a desired shape.

Figure 8A:
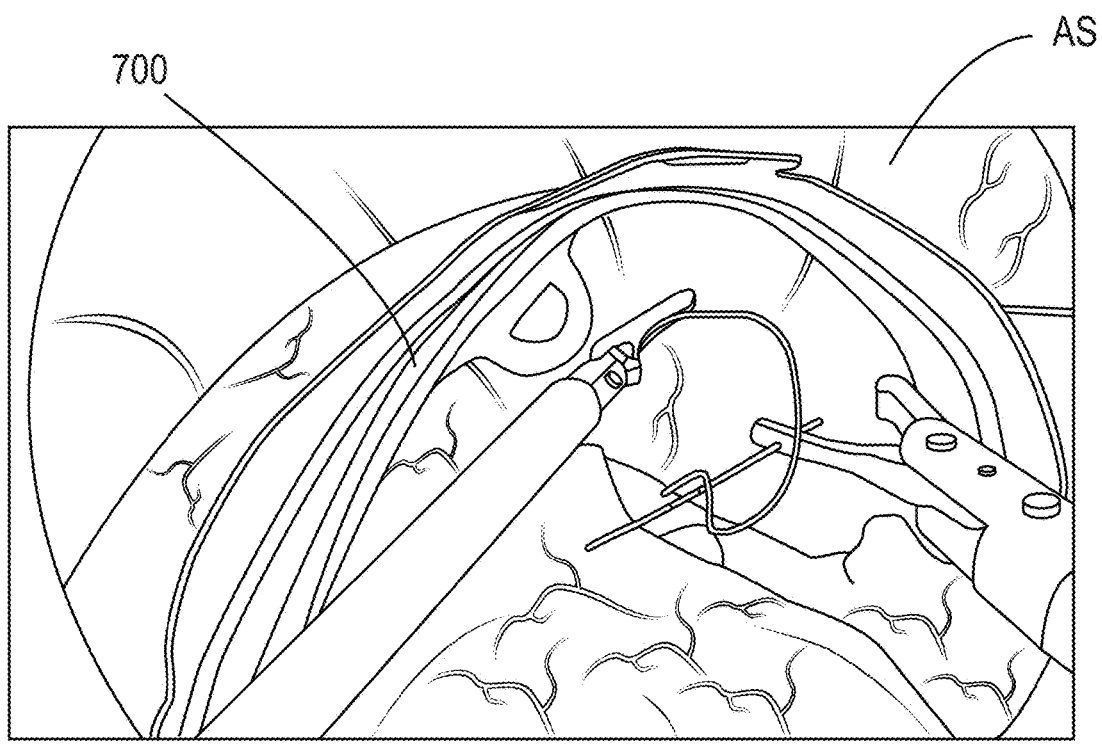
FIGS. 8A and 8B show the exemplary retraction device of FIG. 7 in a patient during an operation.
Figure 8B:
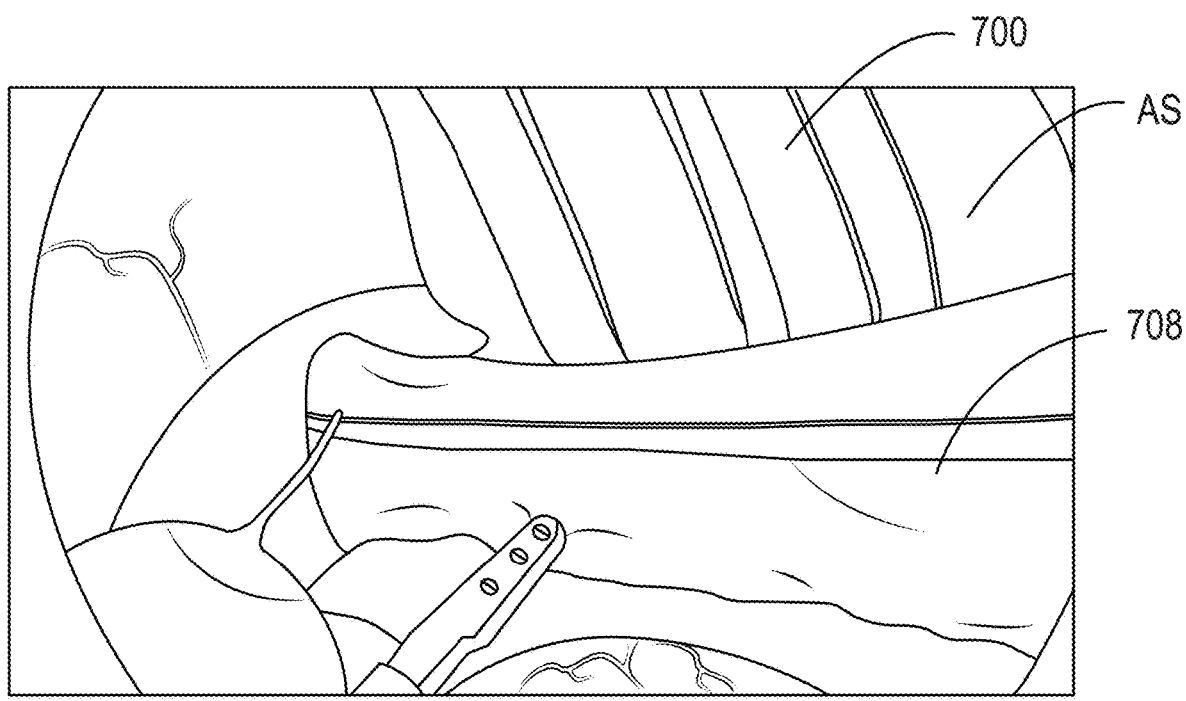

FIGS. 8A and 8B show retraction device 700 in a rigid state, whereby anatomical structure AS is retracted, e.g., lifted, during an operation, thereby providing increased visibility to the surgeon during the operation. As shown in FIGS. 8A and 8B, the surgeon has freedom to use both hands to operate surgical tools during the operation.

Figure 9:
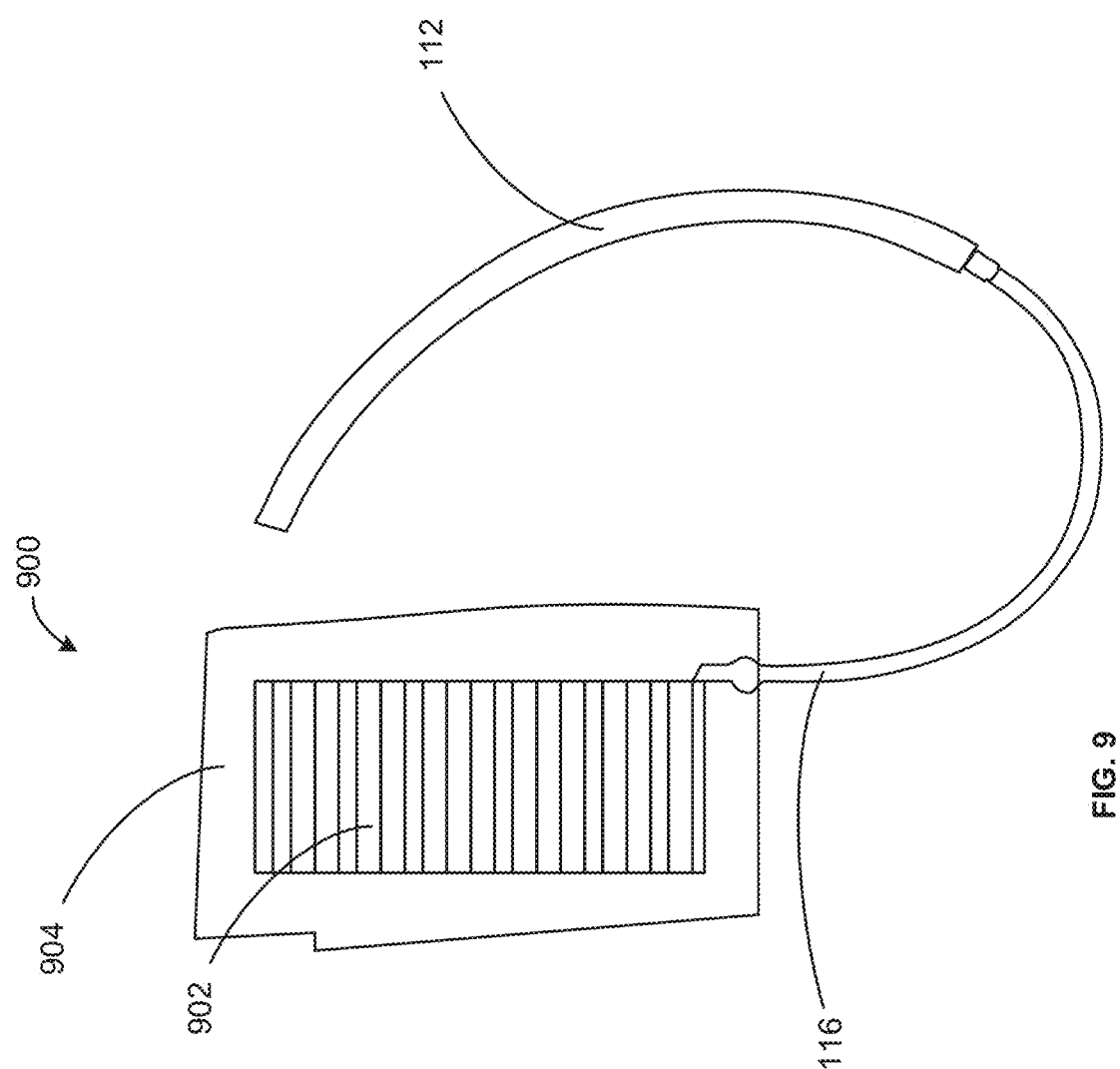
FIG. 9 illustrates another exemplary retraction device constructed in accordance with the principles of the present disclosure.

Referring now to FIG. 9, another exemplary retraction device is described. Retraction device 900 is designed with the ability to change stiffness states without changing size, adding anchors to equipment's outside the human body, needing additional surgical personnel to maintain retraction during surgery, or introducing any additional material. Retraction device 900 includes one or more strips of compliant jammable layer components 902, and may be encapsulate by flexible envelop 904. As shown in FIG. 9, flexible envelop 904 may be translucent, and the strips of compliant jammable layer components 902 may be connected in parallel. In an unjammed, malleable state, retraction device 900 may be manipulated, e.g., deformed about the longitudinal axis or lateral axis of compliant jammable layer components 902.

Figure 10:
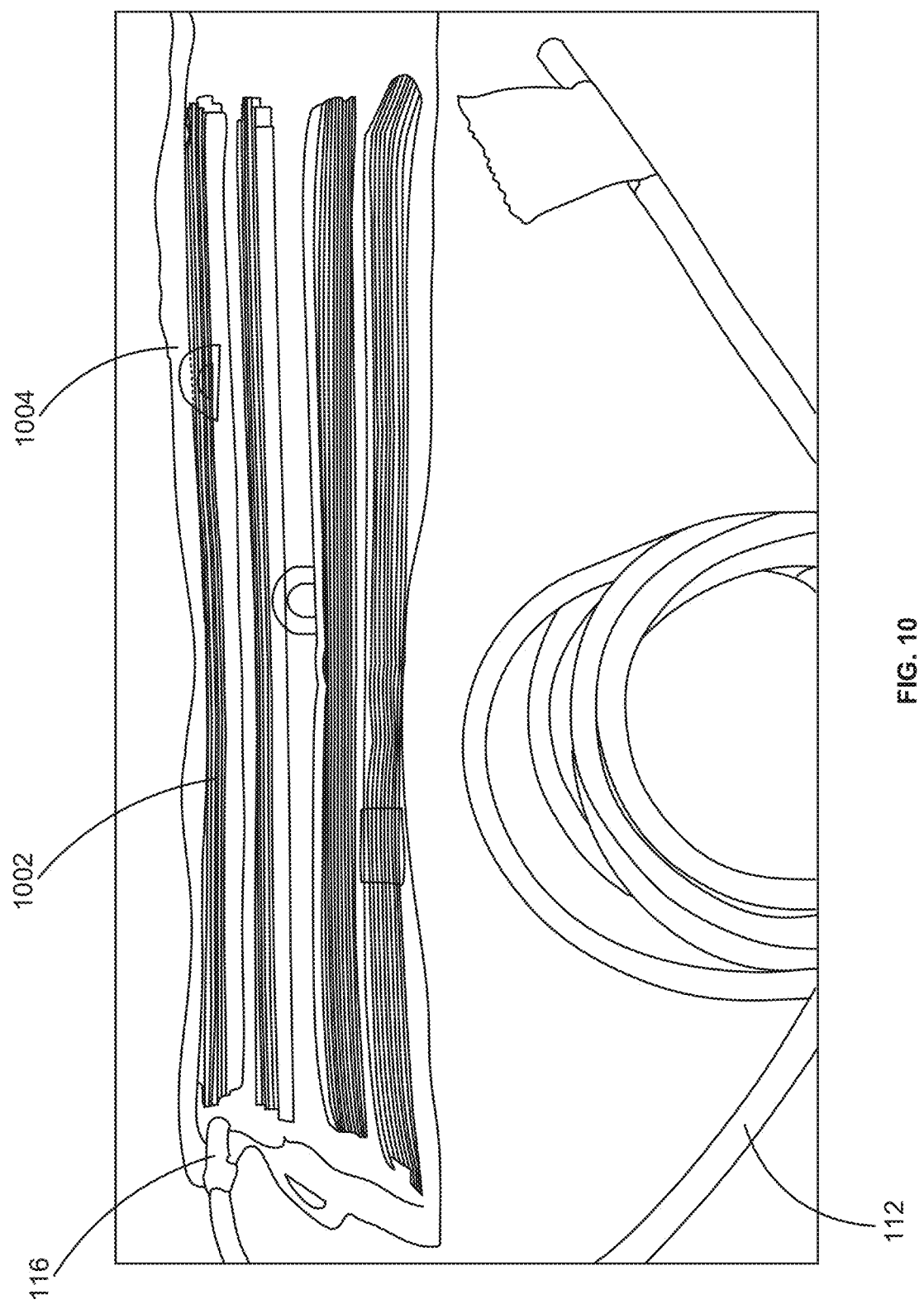
FIG. 10 illustrates yet another exemplary retraction device constructed in accordance with the principles of the present disclosure.

Referring now to FIG. 10, another exemplary retraction device is described. Retraction device 1000 is constructed similar to retraction device 200 of FIG. 2A. As shown in FIG. 10, retraction device 1000 may include four strips of compliant jammable layer components 1002, and may be encapsulated by flexible envelop 1004. As shown in FIG. 10, flexible envelop 1004 may be translucent.

Figure 11:
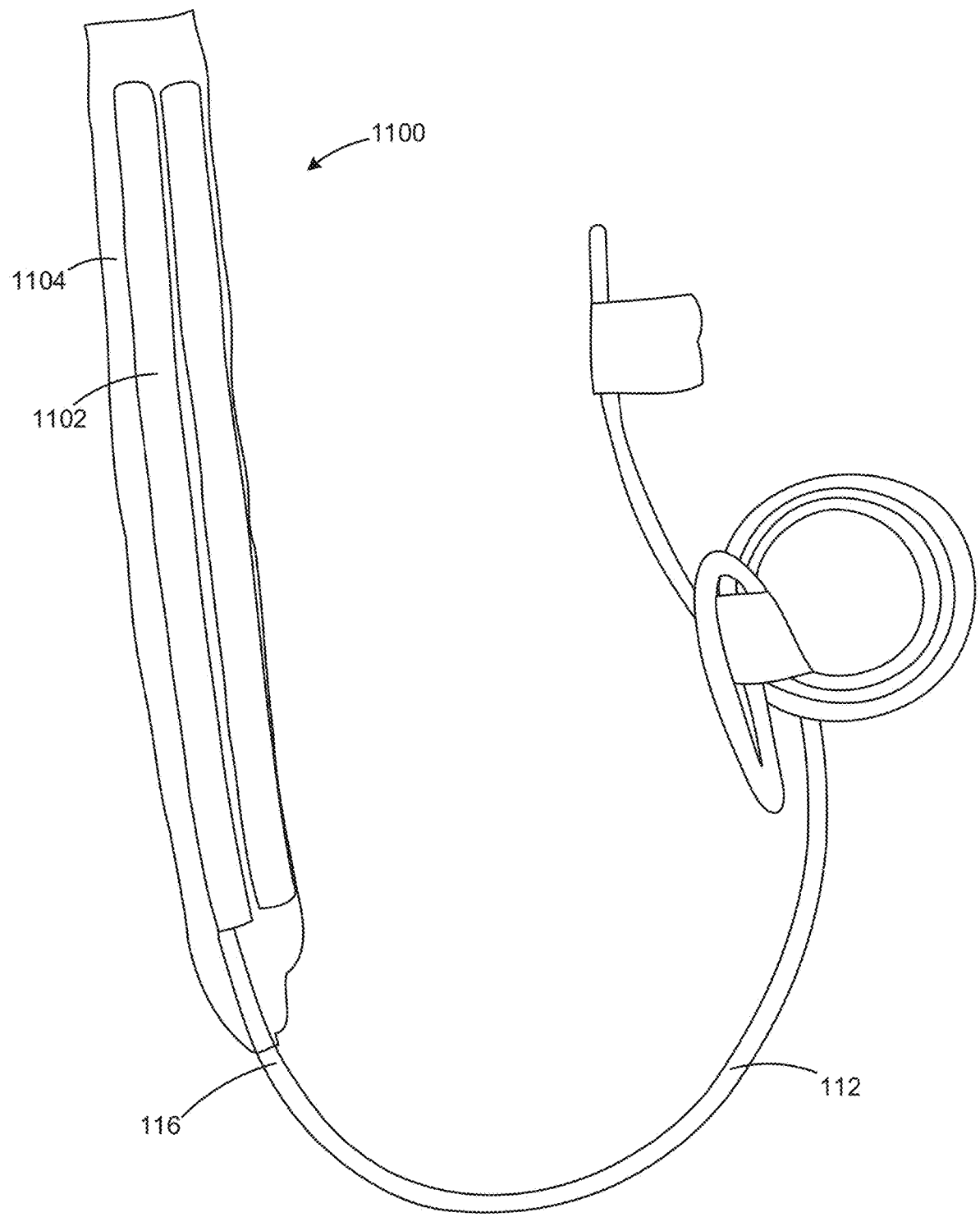
FIG. 11 illustrates yet another exemplary retraction device constructed in accordance with the principles of the present disclosure.

Referring now to FIG. 11, another exemplary retraction device is described. Retraction device 1100 is constructed similar to retraction device 200 of FIG. 2A and retraction device 1000 of FIG. 10. As shown in FIG. 11, retraction device 1100 may include two strips of compliant jammable layer components 1102, and may be encapsulated by flexible envelop 1104. As shown in FIG. 11, flexible envelop 1104 may be translucent.

As will be understood by a person having ordinary skill in the art, more or less strips of compliant jammable layer components may be used depending on the amount of support required specific to the anatomical structures to be retracted. In addition, two pneumatic channels may be connected to the end of the envelope through which a negative pressure (vacuum) and positive pressure can be applied. Pneumatic pouches on either ends of the device may be incorporated to ensure safe contact with surrounding tissue while maintaining the desired shape. The retraction devices described herein may include handles disposed along the retraction device to facilitate manipulation thereof, and tapered end portions to facilitate removal of the retraction device through a trocar as described above. All together this allows the retraction device to be manipulated into a specific shape while in the un-vacuumed state and hold the shape when vacuum is applied.

In accordance with the principles of the present disclosure, the device and methods described herein may be used in a broader field of surgery. Thus, this disclosure also provides methods of surgical intervention using an embodiment of the devices as disclosed herein, on a subject, that may be an animal, a mammal, or a human. Kits containing the device with instructions for use thereof are further provided herein.

While various illustrative embodiments of the invention are described above, it will be apparent to one skilled in the art that various changes and modifications may be made therein without departing from the invention. The appended claims are intended to cover all such changes and modifications that fall within the true scope of the invention.

What is claimed:

1. A method for providing increased visibility during an operation, the method comprising:
   introducing a retraction device in a delivery state to an operation site in a patient, the retraction device comprising one or more strips of compliant jammable layer components, the one or more strips of compliant jammable layer components connected in parallel and encapsulated within a flexible envelop;
   manipulating the one or more strips of compliant jammable layer components to a desired shape; and
   applying negative pressure to the flexible envelope to jam the one or more strips of compliant jammable layer components, such that the retraction device transitions from a malleable state to a rigid state,
   wherein the retraction device, in the rigid state, comprises a stiffness sufficient to retract an anatomical structure of the patient to provide increased visibility of the operation site during the operation.

2. The method of claim 1, wherein the retraction device further comprises an inflatable positive pressure chamber disposed along at least a portion of the retraction device adjacent the flexible envelope.

3. The method of claim 2, further comprising applying positive pressure to the inflatable positive pressure chamber after introducing the retraction device, such that the retraction device transitions from the delivery state to an expanded state.

4. The method of claim 3, further comprising deflating the inflatable positive pressure chamber prior to manipulating the one or more strips of compliant jammable layer components to the desired shape.

5. The method of claim 2, further comprising applying positive pressure to the inflatable positive pressure chamber after manipulating the one or more strips of compliant jammable layer components to the desired shape to increase normal forces on a surface of the retraction device, thereby increasing friction forces between the retraction device and the anatomical structure of the patient.

6. The method of claim 5, further comprising deflating the inflatable positive pressure chamber after applying negative pressure to the flexible envelope, thereby providing stronger retraction of the anatomical structure of the patient during the operation.

7. The method of claim 2, wherein the retraction device comprises a tapered end portion configured to facilitate introduction through a trocar, the method further comprising removing the retraction device by pulling the retraction device through the trocar via the tapered end portion.

* * * * *